United States Patent [19]

Ho et al.

[11] Patent Number: 4,904,477
[45] Date of Patent: Feb. 27, 1990

[54] SPRAY DRIED IBUPROFEN COMPOSITIONS

[75] Inventors: Ying T. R. Ho, Haddonfield; Robert G. Blank, Vineland, both of N.J.

[73] Assignee: American Home Products Corporation, New York, N.Y.

[21] Appl. No.: 378,480

[22] Filed: Jul. 13, 1989

Related U.S. Application Data

[63] Continuation of Ser. No. 71,116, Jul. 8, 1987, abandoned.

[51] Int. Cl.⁴ ................................................. A61K 9/20
[52] U.S. Cl. ..................................... 424/465; 424/479; 424/492; 424/494; 424/497; 424/498
[58] Field of Search ............... 424/465, 479, 480, 492, 424/494, 497, 498

[56] References Cited

U.S. PATENT DOCUMENTS

| | | | |
|---|---|---|---|
| 3,145,146 | 8/1964 | Lieberman et al. | 424/465 |
| 3,382,150 | 5/1968 | Grass | 424/465 |
| 4,143,129 | 3/1979 | Marsden | 424/80 |
| 4,344,934 | 8/1982 | Martin et al. | 424/80 |
| 4,423,027 | 12/1983 | Simon et al. | 424/480 |
| 4,439,453 | 3/1984 | Vogel | 424/465 |
| 4,555,399 | 11/1985 | Hsiao | 424/465 |
| 4,601,895 | 7/1986 | Streuff et al. | 424/479 |
| 4,609,675 | 9/1986 | Franz | 514/568 |
| 4,612,319 | 9/1986 | King | 514/305 |
| 4,661,521 | 4/1987 | Salpekar et al. | 424/465 |
| 4,666,703 | 5/1987 | Kopf | 424/465 |
| 4,670,251 | 6/1987 | Blanco | 424/465 |
| 4,681,765 | 7/1987 | Gruley | 424/455 |
| 4,684,516 | 8/1987 | Bhutani | 424/471 |
| 4,684,524 | 8/1987 | Eckenhoff et al. | 424/469 |
| 4,716,041 | 12/1987 | Kjornaes et al. | 424/468 |

FOREIGN PATENT DOCUMENTS 0040472 11/1981 European Pat. Off. .
0130683 1/1985 European Pat. Off. .

Primary Examiner—Mark L. Bell
Assistant Examiner—David M. Brunsman
Attorney, Agent, or Firm—John W. Routh

[57] ABSTRACT

A spray dried ibuprofen composition suitable for direct compression into tablets comprising a spray dried dispersion in water of ibuprofen, pregalatinized starch, a disintegrant and a wetting agent for the ibuprofen.

7 Claims, No Drawings

SPRAY DRIED IBUPROFEN COMPOSITIONS

This application is a continuation of application Ser. No. 071,116, filed July 8, 1987, now abandoned.

BACKGROUND OF THE INVENTION

The invention relates to spray dried compositions comprising agglomerates of ibuprofen in a gelatinized starch matrix and to a method for manufacture thereof.

The commercial analgesic, aspirin, can be dry-mixed with starch and is then directly compressible into tablets. The commercial analgesic acetaminophen, on the other hand, cannot be similarly dry mixed and directly compressed but must be further processed such as, for example, by wet granulation; by spray drying acetaminophen with pre-gelatinized starch as described in European Pat. Appln. EP 40,472; or by fluidizing acetaminophen and cross-linked sodium carboxymethyl cellulose in hot air, pulverizing the mixture with pregelatinized starch paste, and drying as described in Fr. Demande FR 2,496,461.

The commercial analgesic ibuprofen is also different from aspirin in that it cannot be dry-mixed with starch and directly compressed into tablets. In the past, most ibuprofen tablets have been prepared from a wet granulation of a binder and ibuprofen which is dried, mixed with lubricants and disintegrating agents and compressed into tablets. This process involves several processing steps and is disadvantageous because of the equipment costs, time involved and higher rejection rate. A dry granulation process is described in U.S. Pat. No. 4,609,675.

SUMMARY OF THE INVENTION

The present invention provides a spray dried ibuprofen composition which is directly compressible into tablets. The spray dried compositions are free flowing and simplify production of tablets to a simple mixing and tabletting operation with the necessity of only small amounts of conventional tabletting lubricants and with a minimal rejection rate of underweight or imperfect tablets. Moreover, tablets formed from the spray dried compositions have good physical stability in respect of friability, disintegration and dissolution properties, and have excellent bioavailability associated with high dosage levels of ibuprofen.

The spray dried ibuprofen compositions of this invention comprise finely divided ibuprofen in a gelatinized starch matrix and are of a generally spherical shape. The spary dried compositions comprise ibuprofen, as a disintegrant crospovidone, croscarmellose sodium and/or sodium starch glycolate, pregelatinized starch, colloidal silica and as a wetting agent polyvinylpyrrolidone and/or sodium lauryl sulfate.

The proportions of ingredients in the spray dried ibuprofen compositions can be adjusted within limits to provide a free flowing, dust free powder suitable for feed to a high speed table press. The proportions generally range from about 80% to about 90% by weight ibuprofen, about 1.5% to about 6% by weight disintegrant, about 8% to about 12% by weight pregelatinized starch, about 0.10% to about 0.35% by weight colloidal silica, and about 0.2% to about 2.0% by weight wetting agent.

The spray dried compositions of the invention have several properties which make them especially suitable for charging to a high speed tablet press. One such property is the free flow characteristic as evidenced by a low angle of repose when collected, for example, in a beaker from a funnel positioned above the beaker. The free flow characteristic permits faster tablet compression with less weight variation between tablets. Another such property is the natural lubricity of the spray dried compositions, requiring only minimal amount of tabletting lubricants such as, for example, stearic acid. In general, the lower the lubricant level, the faster the dissolution of the tablet.

DETAILED DESCRIPTION OF THE INVENTION

The ibuprofen is available commercially, for example, from Ethyl Corporation, Baton Rouge, La. A suitable pharmaceutical grade is marketed as a powder with a particle distribution of 100–250 microns.

Croscarmellose sodium is a cross-linked polymer of carboxymethylcellulose sodium and is available in Type A and Type B depending upon the degree of substitution. Type A is preferred for the compositions of this invention. It is sold under the trade name ACDISOL and is available from FMC Corporation, 200 Market Street, Philadelphia Pa. 19103, U.S.A.

Pregelatinized starch is starch that has been chemically and/or mechanically processed to rupture all or part of the granules separated from thematuregrain of corn in the presence of water. It is available from National Starch and Chemical Corp., Bridgewater, N.J. U.S.A. as STARCH 1551.

The colloidal silica is a commercial product and is available commercially in USP and NF grades. It is marketed by Degussa Corp., Teterboro, N.J. U.S.A. and a suitable grade is marketed under the tradename AEROSIL 200.

Polyvinylpyrrolidone is available commercially in U.S.P. grade under the generic name povidone and is marketed by GAF Corporation, 140 West 51st. Street, New York, N.Y. 10020 under the trademark PLASDONE K. A suitable grade is PLASDONE K-29/32 which has a molecular weight of about 29,000–32,000. Crospovidone are cross linked insoluble homopolymers of polyvinylpyrrolidone also known as polyvinylpolypyrrolidone. It is also available from GAF Corporation under the trademark POLYPLASDONE-XL-X.

Sodium lauryl sulfate is a commercial product in USP grade. Preferably it is used in powder form to promote blending and is available from Albright Wilsen, 180 Old Tappan Road, Old Tappan, N.J., U.S.A., under the tradename EMPICOL, and a suitable grade is EMPICOL 0303. Sodium starch glycolate is available commercially and is marketed by Generichem Corp., 85 Main Street, Little Falls, N.J. under the trademark PRIMOJEL.A. It is made from potato starch.

Spray dryers can be of the usual laboratory or commercial type. Suitable spray dryers are manufactured by Buchi Laboratoriums-Technik AG, by the Anhydro Company of Attleboro, Mass. and Niro Atomizer Inc., of Columbia, Md.

The spray dryer employed in the first six examples was a Niro Portable Spray Dryer, Model No. 21231-0001. The operating conditions include a variable air inlet temperature, a variable air pressure of compressed air driving the atomizer wheel, and a variable feed rate.

The invention will be further illustrated by the following examples in which the spray dried compositions were prepared using the procedure described therein.

In the examples where indicated there were employed ibuprofen, STARCH 1551 brand of pregelatinized starch, AEROSIL 200 brand of colloidal silica, AC-DISOL Type A brand of croscarmellose sodium and PLASDONE K-29/32 brand of povidone, EMPICOL 0303 brand of sodium lauryl sulfate, and PRIMOJEL brand of sodium starch glycolate.

The invention will be further illustrated by the following examples in which the spray dried compositions were prepared using the procedures described therein.

EXAMPLE 1

In this example the feed mixture charged to the spray dryer was composed of the following materials.

| Ingredient | Grams Ingredient | Weight % Ingredient in Suspension | Weight % Ingredient in Powder |
| --- | --- | --- | --- |
| Ibuprofen | 1000 | 35.9 | 85 |
| Pregelatinized Starch | 140 | 4.0 | 11.9 |
| Croscarmellose Sodium | 28 | .77 | 2.4 |
| Colloidal Silica | 3 | .08 | 0.26 |
| Povidone | 5 | .14 | 0.43 |
| Purified Water, deionized | 2414 | | |
| | 3590 | | |

The water was placed in a stainless steel mixing vessel equipped with a Lightnin mixer. The povidone, croscarmellose sodium, and colloidal silica were slowly added to the water with mixing and mixing was continued for 5 minutes. The ibuprofen powder was slowly dispersed in the mixture and mixed for 30 minutes until homogeneous. The pregellatinized starch was then slowly added and mixed until homogeneous.

The spray dryer was operated with a feed rate of 30 to 35 grams per minute and an air outlet temperature of 60° to 65° C. The atomizer pressure was 2.2 to 2.3 bar.

The product from the spray dryer was a fine powder with a moisture content of 1.17%.

EXAMPLE 2

In this example the feed mixture charged to the spray dryer was composed of the following materials.

| Ingredient | Grams Ingredient | Weight % Ingredient in Suspension | Weight % Ingredient in Powder |
| --- | --- | --- | --- |
| Ibuprofen | 500 | 23.94 | 85 |
| Pregelatinized Starch | 50 | 2.39 | 8.5 |
| Croscarmellose Sodium | 35 | 1.67 | 5.94 |
| Colloidal Silica | 1.5 | .07 | 0.25 |
| Povidone | 2 | .09 | 0.34 |
| Purified Water, deionized | 1500 | | 100% |
| | 2088.5 | | |

The water was placed in a stainless steel mixing vessel equipped with a Lightnin mixer. Slowly added to the water with mixing were the croscarmellose sodium, the colloidal silica and the povidone. Mixing was continued for 5 minutes. The ibuprofen was then slowly added to the mixture and mixing was continued for 30 minutes. The pregelatinized starch was then added and mixing continued for 20 minutes.

The spray dryer was operated with a feed rate of 20-25 grams per minute and the air inlet heater was set to produce an air outlet temperature of 60°-65° C. The atomizer pressure was 4 bar.

The product from the spray drier was a fine powder.

EXAMPLE 3

In this example the feed mixture charged to the spray dryer was composed of the following materials.

| Ingredient | Grams Ingredient | Weight % Ingredient in Powder |
| --- | --- | --- |
| Ibuprofen | 500 | 85 |
| Pregelatinized Starch | 62.5 | 10.63 |
| Croscarmellose Sodium | 20.0 | 3.40 |
| Colloidal Silica | 1.5 | 0.17 |
| Povidone | 4.0 | 0.68 |
| Purified Water, deionized | 1512 | 100% |
| | 2100 | |

The water was placed in a stainless steel mixing vessel equipped with a Lightnin mixer. Slowly added to the water with mixing were the croscarmellose sodium, the colloidal silica and the providone. Mixing was continued for 5 minutes. The ibuprofen was then slowly added to the mixture and mixing was continued for 30 minutes. The pregelatinized starch was then added and mixing continued for 2 hours.

The spray dryer was operated with a feed rate of 30 grams per minute and the air inlet heater was set to produce an air outlet temperature of 60°-65° C. The atomizer pressure was 80 p.s.i.

The product from the spray drier was a fine powder of about 40 microns with a moisture content of 0.4% and a bulk density of 0.401 grams per cubic centimeter.

The above spray dried powder was blended into a formulation for a compressed tablet as follows:

| | Grams Per Batch | Milligrams Per Tablet |
| --- | --- | --- |
| Spray Dried Powder (85% ibuprofen) | 152.95 | 235.3 |
| Croscarmellose Sodium, Type A | 9.75 | 15.0 |
| Pregelatinized Starch | 19.50 | 30.0 |
| Compressible starch | 16.25 | 25.0 |
| Colloidal Silica | 0.13 | 0.2 |
| Sodium lauryl sulfate | 0.33 | 0.5 |
| Stearic acid | 1.30 | 2.0 |
| | | 308.0 |

The compression mix for tabletting was prepared by separately mixing the spray dried powder with the croscarmellose sodium, the pregellatinized starch and the compressible starch for 10 minutes in a PK-blender and then mixing with a pre-screened (30 mesh Tyler) mixture of the colloidal silica, the sodium lauryl sulfate and the stearic acid powder.

The compression mix was tabletted on a Stokes Rotary Press using tablet tooling set up for double compression with a release pressure of 2.6 tons at a RPM of 14. The compression mix showed good flow characteristics.

The tablets were divided into two batches and the physical characteristics of the tablets are shown below:

| | Batch 1 | Batch 2 |
| --- | --- | --- |
| Average weight, mg/tab | 308–309 | 308–310 |
| Thickness, inch | 0.206–0.208 | 0.206–0.208 |
| Hardness, Strong Cobb Units | 6–8 | 4–6 |
| Disintegration Time, minutes | 1.25–1.50 | 1.25 |

-continued

|  | Batch 1 | Batch 2 |
|---|---|---|
| Friability, USP Test | 0–0.1 | 0–0.1 |

EXAMPLE 4

In this example the feed mixture charged to the spray dryer was composed of the following materials.

|  | Grams Ingredient | Weight % Ingredient in Powder |
|---|---|---|
| Ibuprofen | 500 | 85 |
| Pregelatinized Starch | 62.5 | 10.63 |
| Sodium Starch Glycolate | 20.0 | 3.40 |
| Colloidal Silica | 1.5 | 0.26 |
| Povidone | 4.0 | 0.68 |
| Purified Water, deionized | 1512 |  |
|  | 2100 |  |

The water was placed in a stainless steel mixing vessel equipped with a Lightnin mixer. Slowly added to the water with mixing were the sodium starch glycolate, the colloidal silica and the povidone. Mixing was continued for 5 minutes. The ibuprofen was then slowly added to the mixture and mixing was continued for 30 minutes. The pregelatinized starch was then added and mixing continued for 1 hour.

The spray dryer was operated with a feed rate of 32 grams per minute and the air inlet heater was set to produce an air outlet temperature of 60°–65° C. The atomizer pressure was 80 p.s.i.

The product from the spray drier was a fine powder of about 40 microns with a moisture content of 0.8% and a bulk density of 0.380 grams per cubic centimeter. The particle size distribution (Tyler screen) was, as percent retained on .100 mesh, 0.5%; retained on 200 mesh, 7.5%; retained on 325 mesh, 68.2% and greater than 325 mesh, 24.2%.

The above spray dried powder was blended into a formulation for a compressed tablet as follows:

|  | Milligrams Per Tablet |
|---|---|
| Spray Dried Powder (85% ibuprofen) | 257.4 |
| Sodium starch glycolate | 10.0 |
| Pregelatinized Starch | 20.0 |
| Compressible starch | 40.0 |
| Magnesium Stearate | 0.8 |
| Stearic acid | 2.0 |
|  | 330.0 |

The compression mix for tabletting was prepared by separately mixing the spray dried powder with the sodium starch glycolate, the pregellatinized starch and the compressible starch for 8 minutes in a PK-blender and then mixing with a pre-screened (30 mesh Tyler) mixture of the magnesium stearate and the stearic acid powder.

The compression mix was tabletted on a Stokes Rotary Press using tablet tooling set up for double compression with a release pressure of 2.6 tons at a RPM of 14. The cmpression mix showed good flow characteristics.

The physical characteristics of the tablets are shown below:

|  | Batch |
|---|---|
| Average weight, mg/tab | 330 |
| Thickness, inch | 0.212–0.216 |
| Hardness, Strong Cobb Units | 4–6 |
| Friability, USP Test | 0–0.1 |

EXAMPLE 5

In this example the feed mixture charged to the spray dryer was composed of the following materials.

|  | Grams Ingredient | Weight % Ingredient in Powder |
|---|---|---|
| Ibuprofen | 500 | 84.96 |
| Pregelatinized Starch | 60 | 10.20 |
| Croscarmellose Sodium | 25 | 4.25 |
| Colloidal Silica | 1.5 | 0.25 |
| Sodium Lauryl Sulfate | 2.0 | 0.34 |
| Purified Water, deionized | 1500 | 100% |
|  | 2088.5 |  |

The water was placed in a stainless steel mixing vessel equipped with a Lightnin mixer. Slowly added to the water with mixing were the croscarmellose sodium, the colloidal silica and sodium lauryl sulfate. Mixing was continued for 5 minutes. The ibuprofen was then slowly added to the mixture and mixing was continued for 30 minutes. The pregelatinized starch was then added and mixing continued for 20 minutes.

The spray dryer was operated with a feed rate of 20–25 milliliters per minute and the air inlet heater was set to produce an air outlet temperature of 60°–63° C. The atomizer pressure was 3.5 bar.

The product from the spray drier was a fine powder.

The above spray dried powder was blended into a formulation for a compressed tablet as follows:

|  | Milligrams Per Tablet |
|---|---|
| Spray Dried Powder (85% ibuprofen) | 235.3 |
| Croscarmellose Sodium, Type A | 20.0 |
| Pregelatinized Starch | 60.0 |
| Colloidal Silica | 0.20 |
| Sodium lauryl sulfate | 0.50 |
| Stearic acid | 2.0 |
|  | 320.0 |

The compression mix for tabletting was prepared by separately mixing the spray dried powder with the croscarmellose sodium, the pregellatinized starch and the compressible starch for 10 minutes in a PK-blender and then mixing with a pre-screened (30 mesh Tyler) mixture of the colloidal silica, the sodium lauryl sulfate and the stearic acid powder.

The compression mix was tabletted on a Stokes Rotary Press using tablet tooling set up for double compression with a release pressure of 2.6 tons at a RPM of 14. The compression mix showed good flow characteristics.

The physical characteristics of the tablets are shown below:

|  | Batch |
|---|---|
| Average weight, mg/tab | 320 |

-continued

|  | Batch |
|---|---|
| Thickness, inch | 0.212–0.215 |
| Hardness, Strong Cobb Units | 4–5 |
| Disintegration Time, minutes | 1–1.25 |
| Friability, USP Test | 0–0.1 |

EXAMPLE 6

In this example the feed mixture charged to the spray dryer was composed of the following materials.

|  | Grams Ingredient | Weight % Ingredient in Powder |
|---|---|---|
| Ibuprofen | 500 | 85.03 |
| Pregelatinized Starch | 50 | 8.5 |
| Croscarmellose Sodium | 35 | 5.59 |
| Colloidal Silica | 1.5 | 0.26 |
| Sodium Lauryl Sulfate | 1.5 | 0.26 |
| Purified Water, deionized | 1400 | 100% |

The water was placed in a stainless steel mixing vessel equipped with a Lightnin mixer. Slowly added to the water with mixing were the croscarmellose sodium, the colloidal silica and the sodium lauryl sulfate. Mixing was continued for 5 minutes. The ibuprofen was then slowly added to the mixture and mixing was continued for 30 minutes. The pregelatinized starch was then added and mixing continued for 20 minutes.

The spray dryer was operated with a feed rate of 15–17 milliliters per minute and the air inlet heater was set to produce an air outlet temperature of 60°–65° C. The atomizer pressure was 3.5 bar.

The product from the spray drier was a fine powder.

The above spray dried powder was blended into a formulation for a compressed tablet as follows:

|  | Milligrams Per Tablet |
|---|---|
| Spray Dried Powder (85% ibuprofen) | 235.3 |
| Croscarmellose Sodium, Type A | 20.0 |
| Pregelatinized Starch | 30.0 |
| Compressible Starch | 20.00 |
| Colloidal Silica | 0.20 |
| Sodium lauryl sulfate | 0.50 |
| Stearic acid | 2.0 |
|  | 308.0 |

The compression mix for tabletting was prepared by separately mixing the spray dried powder with the croscarmellose sodium, the pregellatinized starch and the compressible starch for 10 minutes in a PK-blender and then mixing with a pre-screened (30 mesh Tyler) mixture of the colloidal silica, the sodium lauryl sulfate and the stearic acid powder.

The compression mix was tabletted on a Stokes Rotary Press using tablet tooling set up for double compression with a release pressure of 2.6 tons at a RPM of 14. The compression mix showed good flow characteristics.

EXAMPLE 7

In this example the feed mixture charged to the spray dryer was composed of the following materials.

|  | Grams Ingredient | Weight % Ingredient in Powder |
|---|---|---|
| Ibuprofen | 500.0 | 88.07 |
| Pregelatinized Starch | 50.0 | 8.81 |
| Crospovidone NF, XL | 10.0 | 1.76 |
| Colloidal Silica | 1.5 | 0.26 |
| Povidone | 6.25 | 1.10 |
| Purified Water, deionized | 1512 | 100% |
|  | 2100 |  |

The water was placed in a stainless steel mixing vessel equipped with a Lightnin mixer. Slowly added to the water with mixing were the crospovidone, the colloidal silica and the povidone. Mixing was continued for 5 minutes. The ibuprofen was then slowly added to the mixture and mixing was continued for 30 minutes. The pregelatinized starch was then added and mixing continued for 2 hours. The change to the spray drier contained 30% solids.

The spray dryer was operated with a feed rate of 30 grams per minute and the air inlet heater was set to produce an air outlet temperature of 60°–65° C. The atomizer pressure was 80 p.s.i.

The product from the spray drier was a fine powder of about 40 microns with a moisture content of 0.4% and a bulk density of 0.401 grams per cubic centimeter.

The above spray dried powder was blended into a formulation for a compressed tablet as follows:

|  | Grams Per Batch | Milligrams Per Tablet |
|---|---|---|
| Spray Dried Powder (88% ibuprofen) | 113.6 | 227.2 |
| Croscarmellose Sodium, Type A | 9.0 | 18.0 |
| Pregelatinized Starch | 15.0 | 30.0 |
| Compressible starch | 15.0 | 30.0 |
| Colloidal Silica | 0.15 | 0.3 |
| Sodium lauryl sulfate | 0.30 | 0.6 |
| Stearic acid | 1.00 | 2.0 |
|  |  | 308.1 |

The compression mix for tabletting was prepared by separately mixing the spray dried powder with the croscarmellose sodium, the pregellatinized starch and the compressible starch for 10 minutes in a PK-blender and then mixing with a pre-screened (30 mesh Tyler) mixture of the colloidal silica, the sodium lauryl sulfate and the stearic acid powder.

The compression mix was tabletted on a Stokes Rotary Press using tablet tooling set up for double compression with a release pressure of 2.6 tons at a RPM off 14. The compression mix showed good flow characteristics.

The tablets were divided into two batches and the physical characteristics of the tablets are shown below:

|  | Batch |
|---|---|
| Average weight, mg/tab | 308–309 |
| Thickness, inch | 0.206–0.209 |
| Hardness, Strong Cobb Units | 4–6 |
| Disintegration Time, minutes | 1–1.5 |
| Friability, USP Test, 4 min. | 0–0.1 |

EXAMPLE 8

In this example, four large size runs were made with an eight foot diameter Bowen Pilot Unit spray dryer. The charges to the runs are shown in the following table in terms of weight percentage of each ingredient and solids content of the dispersion to the spray dryer.

Typically, the solids were added to the water in the Dryer Feed Slurry Make-up Tank and agitated for two hours. The final viscosity ranged between 175-200 cps, the temperature between 24°-26° C., and the pH about 5.4

The spray dryer was operated at an air inlet temperature of 138°-143° C., an air outlet temperature of 60°-65° C., an atomizer RPM of 19,000-21,000 and a feed rate of about 120 pounds per hour. The yield was about 95%.

The spray dried powder from Run 1 typically had a loose bulk density of 0.372 grams per cubic centimeter, a moisture content of 1.0 per cent, and a sieve fraction % Alpine retained on +200 mesh of 14.9, and retained on +325 mesh of 49.0.

The spray dried powder from Run 2 typically had a loose bulk density of 0.354 grams per cubic centimeter, a moisture content of 0.86 per cent, and a sieve fraction % Alpine retained on +200 mesh of 13.5 and retained on +325 mesh of 42.0. The flow rate through the bulk densiometer was 43 seconds and the angle of repose was 39°.

The spray dried powder from Run 3 typically had a loose bulk density averaging 0.359 grams per cubic centimeter, a moisture content averaging 0.95 per cent, and a sieve fraction % Alpine retained on +200 mesh averaging 12.1 and retained on +325 mesh averaging 39.1.

The spray dried powder from Run 4 typically had a loose bulk density averaging 0.362 grams per cubic centimeter, a moisture content of 1.19 and a sieve fraction % Alpine retained on +200 mesh of 4.1 and retained on +325 mesh of 25.1. The flow rate through the bulk densiometer was 42 seconds and the angle of repose was 39°.

|  | Run #1 | | Run #2 | | Run #3 | | Run #4 | |
|---|---|---|---|---|---|---|---|---|
| Ingredient | Percent | Weight Kilograms | Percent | Weight Pounds | Percent | Weight Kilograms | Percent | Weight Kilograms |
| Pregelantinized Starch | 10.00% | 9.091 | 10.47 | 20.94 | 10.25 | 8.441 | 10.25 | 8.441 |
| Croscarmellose Sodium | 3.50% | 3.182 | 3.41 | 6.82 | 3.50 | 2.882 | 3.50 | 2.882 |
| Colloidal Silica | 0.30% | 0.273 | 0.27 | 0.54 | 0.25 | 0.206 | 0.25 | 0.206 |
| Povidone | 1.20% | 1.091 | 0.85 | 1.70 | 1.00 | 0.824 | 1.00 | 0.824 |
| Ibuprofen | 85.00% | 77.274 | 85.00 | 170.00 | 85.00 | 70.0 | 85.00 | 70.0 |
| Total | 100.00% | 90.91 | 100% | 200.00 | 100% | 82.553 | 100% | 82.353 |
| Deionized, Filtered Water | 56 gallons | | 56 gallons | | 51 gallons | | 51 gallons | |
| Percent Solids | 30% Solids | | 30% Solids | | 30% Solids | | 30% Solids | |

EXAMPLE 9

In this example, a semi-production run was made on the Bowen Pilot Unit spray dryer used in the previous example. The dry ingredients in the charge to the spray dryer, as shown below, were dry blended in a PK blender for 30 minutes.

| Ingredient | Percent | Weight Kilograms |
|---|---|---|
| Pregelatinized Starch | 10.25 | 41.0 |
| Croscarmellose Sodium | 3.50 | 14.0 |
| Colloidal Silica | 0.25 | 1.0 |
| Povidone | 1.00 | 4.0 |
| Ibuprofen | 85.00 | 340.0 |
| Total | 100.00% | 400.0 |
| Deionized, Filtered Water | 246 gallons | |
| Percent Solids | 30% | |

The solids were added to the water in the Dryer Feed Slurry Make-up Tank and agitated for 55 hours.

After 42 hours 10 additional gallons of water were added to the tank to maintain the solids content at about 30%. The final viscosity ranged between 500 to 750 cps, the temperature between 22.2 and 32.2° C. and the pH was 5.47.

The spray dryer was charged over a single day period from 1127 until 1647 hours. The spray dryer was operated at an air inlet temperature of 270°-275° F., an air outlet temperature of about 140° F., an atomizer RPM of 18,639 and a feed rate of about 0.77-0.82 gallons per minute. The yield was about 95%.

Samples of product from the spray dryer were taken periodically and the loose bulk density, moisture content and particle size distribution are shown in the following table. The spray dried material was collected into 7 drums.

| Time | Moisture % | LBD g/cc | Sieve +200 | Fraction +325 | |
|---|---|---|---|---|---|
| 1127 | .73 | .350 | 9.8 | 34.1 | |
| 1147 | 1.0 | .354 | 14.0 | 37.2 | Drum 1 |
| 1207 | 0.96 | .356 | 10.9 | 38.6 | |
| 1233 | 0.98 | .353 | 16.3 | 41.2 | |
| 1253 | | | 16.6 | 42.9 | |
| 1314 | .93 | .349 | 15.6 | 43.2 | Drum 2 |
| 1334 | | | | | |
| 1346 | .89 | .360 | 17.7 | 44.3 | |
| 1415 | .86 | .356 | 15.8 | 42.0 | |
| 1435 | .91 | .340 | 12.5 | 41.3 | Drum 3 |
| 1500 | | | | | |
| 1520 | .88 | .344 | 10.4 | 42.7 | Drum 4 |
| 1540 | | | 14.5 | 43.3 | |
| 1600 | .91 | .343 | 11.8 | 40.5 | |
| 1630 | .90 | .341 | 10.8 | 39.5 | Drum 5 |
| 1650 | .88 | .340 | 10.0 | 37.9 | |
| 1720 | 1.06 | .334 | 15.2 | 40.5 | Drum 6 |
| 1740 | | .350 | 20.6 | 46.0 | |
| 1810 | .93 | .349 | 17.1 | 48.4 | Drum 7 |
| 1830 | | | | | |

The flow rate, as measured in seconds required to empty a funnel having a top opening of four and one-quarter inches in diameter, a bottom opening of three-quarter inch in diameter and a height of 12 inches, was determined and the angle of repose was determined by collecting the flow from the funnel in a 400 milliliter Nalgene beaker placed 4 inches below the funnel, the beaker having a top diameter of 3⅞ inches, a bottom diameter of 2⅞ inches and a height of 4⅝ inches, measuring the distance from the top of the beaker to the top of the powder, and extrapolating from a conversion table. The results are shown below:

|  | Spray Dried Powder | | |
| --- | --- | --- | --- |
|  | Flow Rate, Seconds | Angle Of (°) Repose | Loose Bulk Density (gm/cc) |
| Drum 1 | 56 | 37 | 0.397 |
| Drum 2 | 47 | 38 | 0.386 |
| Drum 3 | 48 | 37 | 0.401 |
| Drum 4 | 43 | 37 | 0.404 |
| Drum 5 | 65 | 39 | 0.395 |
| Drum 6 | 43 | 36 | 0.404 |
| Drum 7 | 35 | 42 | 0.395 |

For optimum tabletting results, the loose bulk density is in the range of about 0.35 to 0.38 grams per cubic centimeter, the moisture content is less than 1% and the particle distribution is such that the sieve fraction % Alpine retained on +200 mesh ranges from about 10 to about 15% and retained on +325 ranges from about 40 to about 60%. The angle of repose is between about 20° to about 50°, preferably about 35° to about 45°.

EXAMPLE 10

Tablets were made from the spray dried powders from Examples 8 and 9 each with the formulation below:

| Ingredient | Milligrams Per Tablet |
| --- | --- |
| Spray Dried Powder | 236.0 |
| Pregelatinized Starch | 22.5 |
| Compressible Starch | 22.5 |
| Croscarmellose Sodium, Type A | 18.0 |

-continued

| Ingredient | Milligrams Per Tablet |
| --- | --- |
| Colloidal Silica | 0.45 |
| Sodium lauryl sulfate | 0.75 |
| Stearic acid | 1.80 |
| Total | 302.0 |

The compression mix for tabletting was prepared by separately mixing the spray dried powder with the croscarmellose sodium, the pregelatinized starch and the compressible starch for 10 minutes in a PK-blender and then mixing with a pre-screened (30 mesh Tyler) mixture of the colloidal silica, the sodium lauryl sulfate and the stearic acid powder. The flow rate through the bulk densiometer, the bulk density and the angle of repose were measured and are shown in the following table.

|  | Compression Mix | | |
| --- | --- | --- | --- |
|  | Flow Rate Seconds | Loose Bulk Density (gm/cc) | Angle of Repose (°) |
| Run 1 | 45 | 0.394 | 36 |
| Run 2 | 38 | 0.398 | 27 |
| Run 3 | — | — | — |
| Run 4 | — | — | — |
| Drum 1 | 46 | 0.459 | 25 |
| Drum 2 | 52 | 0.476 | 18 |
| Drum 3 | 48 | 0.454 | 29 |
| Drum 4 | 33 | 0.423 | 27 |
| Drum 5 | 49 | 0.463 | 21 |
| Drum 6 | 42 | 0.453 | 25 |
| Drum 7 | 46 | 0.461 | 26 |

The compression mix was tabletted on a Stokes Rotary Press using tablet tooling set up for double compression with a release pressure of 2.6 tons at a RPM of 14. The compression mix showed good flow characteristics.

The physical characteristics of the tablets are shown below:

|  | Example 8 | | | | Example 9 |
| --- | --- | --- | --- | --- | --- |
|  | Run 1 | Run 2 | Run 3 | Run 4 | Drum 2 |
| Average weight, mg/tablet | 298 | 298 | 297 | 297 | 300 |
| Thickness, inch | 0.209–0.212 | 0.210–0.212 | 0.207–0.210 | 0.208–0.211 | 0.206–0.211 |
| Hardness, Strong Cobb Units | 4.5–6.5 | 5.5–6.5 | 4.5–5.5 | 4.0–5.5 | 5.5–6.5 |
| Disintegration Time, minutes | 1.75–2 | 1.41–1.67 | 3–4 | 4.75–5.25 | 2–2.25 |
| Dissolution Rate, minutes* | 5 | 4 | 5.6 | 6 | 4 |
| Friability, USP | — | 0.17 | 1.176 | — | — |
| A Friability Stress | — | — | 0.5 | — | 0.5 |

*Dissolution By FDA Method.
Ibuprofen Tablets, Capsules & Caplets
(Time for 80% to be dissolved)

EXAMPLE 11

Tablets were made from the spray dried powders from Example 10, Drums 5, 3 and 4 respectively, from the following ingredients in the amounts listed.

|  | Run #1 | | Run #2 | | Run #3 | |
| --- | --- | --- | --- | --- | --- | --- |
|  | Milligrams Weight | | Milligrams Weight | | Milligrams Weight | |
| Ingredient | Per Tablet | Grams | Per Tablet | Grams | Per Tablet | Grams |
| Spray Dried Powder | 236.00 | 6726 | 236.00 | 7080 | 236.00 | 7080 |
| Pregellatinized Starch | 22.40 | 641.25 | 25.00 | 750 | 25.00 | 750 |
| Starch | — | — | 19.80 | 600 | 24.80 | 600 |
| Compressible Modified Starch | 22.40 | 641.25 | — | — | — | — |
| Croscarmellose Sodium, Type A | 18.00 | 513 | 18.00 | 540 | — | — |
| Crospovidone XL | — | — | — | — | 13.00 | 540 |

|  | Run #1 Milligrams Weight | | Run #2 Milligrams Weight | | Run #3 Milligrams Weight | |
|---|---|---|---|---|---|---|
| Ingredient | Per Tablet | Grams | Per Tablet | Grams | Per Tablet | Grams |
| Colloidal Silica | 0.65 | 14.25 | 0.65 | 13.5 | 0.65 | 13.5 |
| Sodium Lauryl Sulfate | 0.75 | 19.95 | 0.75 | 22.5 | 0.75 | 22.5 |
| Stearic Acid, TP | 1.80 | 51.3 | 1.80 | 54 | 1.80 | 54 |
|  | 302.00 | | 302.00 | | 302.00 | |

The spray dried powder was screened through a #12 mesh screen and added to a PK blender, followed by the pregelatinized starch, the compressible starch, the croscarmellose sodium or crospovidone, and the mixture was blended for 8 minutes. The colloidal silica, sodium lauryl sulfate and the stearic acid were screened through a #30 mesh screen, added to the PK blender and blended for 9 minutes. The flow rate, the loose bulk density and the angle of repose of the compression were measured and are shown below.

|  | | Compression Mix | |
|---|---|---|---|
|  | Flow Rate | Angle of Repose | Loose Bulk Density |
| Run 1 | 49 | 21 | 0.403 |
| Run 2 | 48 | 29 | 0.454 |
| Run 3 | 33 | 27 | 0.423 |

The compression mix was tabletted on a Stokes Rotary Press Model BB-2, a 35 station press with 10.5 millimeter (0.71 concavity) tooling at 14 RPM for one hour and 30 minutes. The compression mix showed good flow characteristics.

The physical characteristics of the tablets are shown below:

|  | Run 1 | Run 2 | Run 3 |
|---|---|---|---|
| Average weight, mg/tablet | 302–305 | 303 | 303 |
| Thickness, inch | 0.203–0.206 | 0.203–0.206 | 0.205–0.209 |
| Hardness, Strong Cobb Units | 5–8 | 5–7 | 6.5–7.5 |
| Disintegration Time, minutes | 2–2.25 | 4.16–4.67 | 2.27–2.40 |
| Dissolution Rate, minutes* | 5.5 | 5 | 6 |
| Friability, USP | 0 | 0 | 0 |
| Content Uniformity | ±3.6% | ±3.61 | ±4.31 |
| Moisture Content, % | 1.31 | 1.38 | 1.88 |

*Dissolution By FDA Method
Ibuprofen Tablets, Capsules
(Time for 80% to be dissolved)

EXAMPLE 12

An 8 kilogram batch of the tablets from Example 11, Run 1 was sugar coated with a coating procedure described below in a Colton 20 inch coating pan rotating at 30 RPM. The various coating materials were poured by hand from a small container or sprayer over the rotating tablets (about 26,500).

A seal coat was applied in the amount of 159 ml from a small sprayer during a period of three minutes. The seal was Opaglos GS-2-0310, a shellac type seal coat marketed by Colorcon Inc. West Point, Pa. After spraying was complete, the tablets were permitted to tumble for 2 minutes and then the tablets were removed from the coating pan and placed in an oven-humidifier at 40° C. for 8 hours. The seal coat was applied in the amount of 0.006 mg/tablet.

A sub coat was applied to 7.5 kilograms of the seal coated tablets (about 24,193). The sub coat contained the ingredients in the amounts listed below:

| Ingredient | Weight Percent | Weight Grams |
|---|---|---|
| Sucrose, NF | 67.3% | 4038 |
| Microcrystalline Cellulose, | 5.2% | 312 |
| Deionized Water | 27.5% | 16.50 |
|  |  | 6000 |

The microcrystalline cellulose was added to the water in a mixing vessel equipped with a stirrer and mixed for 2 minutes at 40 RPM. The suspension was heated to 60° C. and the sucrose was added while mixing. The suspension was maintained at 60°–65° during the time the sub coat was applied in about 18 applications of 200 ml per application, each application being followed by a tumbling period of 10 minutes followed by a warm (30°–35°) air drying interlude of 5 minutes.

The average tablet weight from the over-humidifier is about 310 milligrams and the target weight for the tablet with the subcoat is 425 milligrams. Beginning with the fifteenth application, tablets were weighed to obtain an average tablet weight prior to the next application.

A coloring coat was next applied in about 14 applications at the rate of 60 ml. per application, each application being followed by a tumbling period of 4 minutes followed by a warm (30°–35°) air drying interlude of 2 minutes. The target average tablet weight is 450 milligrams. The coloring coat was a mixture of ingredients in the amounts shown below:

| Ingredient | Weight Percent | Weight Grams |
|---|---|---|
| Sucrose, NF | 63.2% | 448 |
| Coloring | 11.7% | 175 |
| Deionized Water | 25.1% | 376.5 |

The water was heated to 60° C. and the sucrose was added with stirring and cooled to 40° C. Add the coloring agent to the solution and mix for 5 minutes. Maintain the solution at 45° C. during the period of application to the tablets.

A polishing step was next employed in which a mixture of Opaglos GS-2-0310 and carnauba wax was applied to the tumbling tablets in an amount respectively of 0.028 and 0.1 milligram per tablet. Tumbling was continued for 30 minutes to complete the tablet coating procedure.

The coated tablets were tested for dissolution characteristics in accordance with the method suggested by the FDA for ibuprofen tablets. This test method differs from the USP test method in that 80% of the ibuprofen is dissolved in 60 minutes at 50 RPM using a Type 2 paddle. The dissolution time was 12 minutes for the coated tablets of this example.

We claim:

1. A spray dried ibuprofen composition in powder form suitable for direct compression into tablets consisting essentially of about 80% to about 90% by weight ibuprofen, about 2% to about 6% by weight of a disintegrant selected from the class consisting of crospovidone, croscarmellose sodium and sodium starch glycolate, about 8% to about 12% by weight pregelatinized starch, and about 0.2% to about 2% by weight of a wetting agent selected from the class consisting of polyvinylpyrrolidone and sodium lauryl sulfate, the powder having been spray dried from a dispersion in water of the ibuprofen, the disintegrant, the gelatinized starch and the wetting agent.

2. The spray dried composition of claim 1 wherein the wetting agent is polyvinylpyrrolidone.

3. The spray dried composition of claim 1 wherein the wetting agent is sodium lauryl sulfate.

4. The spray dried composition of claim 1 wherein the disintegrant is croscarmellose sodium.

5. A compression mix for compressed tablets containing ibuprofen consisting essentially of, as the ibuoprofen component, the spray dried ibuprofen composition in powder form of claim 1, and additionally containing starch, a disintegrant and a wetting agent.

6. In a coated compressed tablet containing ibuprofen, the improvement which comprises incorporating into the compressed tablet as the ibuprofen component the spray dried ibuprofen composition of claim 5.

7. The improved coated compressed tablet of claim 6 wherein the tablet is a sugar coated compressed tablet.

* * * * *